(12) United States Patent
Small

(10) Patent No.: US 7,001,444 B2
(45) Date of Patent: Feb. 21, 2006

(54) AUTOMATED DUST CONTROL METHOD

(75) Inventor: Terrence P. Small, Downingtown, PA (US)

(73) Assignee: GE Betz, Inc., Trevose, PA (US)

( * ) Notice: Subject to any disclaimer, the term of this patent is extended or adjusted under 35 U.S.C. 154(b) by 53 days.

(21) Appl. No.: 10/467,474

(22) PCT Filed: Feb. 20, 2002

(86) PCT No.: PCT/US02/05034

§ 371 (c)(1),
(2), (4) Date: Jul. 29, 2003

(87) PCT Pub. No.: WO02/069069

PCT Pub. Date: Sep. 6, 2002

(65) Prior Publication Data

US 2004/0216608 A1    Nov. 4, 2004

Related U.S. Application Data

(60) Provisional application No. 60/271,046, filed on Feb. 23, 2001.

(51) Int. Cl.
*B01D 37/04* (2006.01)

(52) U.S. Cl. .......... 95/8; 73/31.02; 73/863.21; 96/417; 340/632

(58) Field of Classification Search .......... 73/31.02, 73/863.21; 95/1, 8; 340/632; 422/88; 96/417
See application file for complete search history.

(56) References Cited

U.S. PATENT DOCUMENTS

| | | | |
|---|---|---|---|
| 4,497,214 A | | 2/1985 | Ramelot ............... 73/863.12 |
| 5,576,739 A | * | 11/1996 | Murphy ................... 340/3.4 |
| 5,667,558 A | * | 9/1997 | Bryan et al. ................ 95/8 |
| 5,667,651 A | * | 9/1997 | Bryan .................... 204/401 |
| 6,114,964 A | | 9/2000 | Fasano .................. 340/632 |
| 6,252,510 B1 | | 6/2001 | Dungan .................. 340/632 |
| 6,369,716 B1 | * | 4/2002 | Abbas et al. ............ 340/632 |

* cited by examiner

*Primary Examiner*—Richard L. Chiesa
(74) *Attorney, Agent, or Firm*—Wegman Hessler & Vanderburg

(57) ABSTRACT

An automated method for suppressing fugitive dust dissemination is disclosed. The method provides for automated measurement of dust levels at remote locations, transmission of the measurements to a centralized monitoring and control system which sends a signal to remote dust suppression treatment application apparatus which apply the appropriate dust suppression treatment chemicals.

5 Claims, No Drawings

AUTOMATED DUST CONTROL METHOD

This application is a national stage of International Application No. PCT/US02/05034, filed on Feb. 20, 2002 and which claims the benefit of Provisional Application Ser. No. 60/271,046, filed on Feb. 23, 2001.

FIELD OF THE INVENTION

The present invention relates to automated methods of suppressing fugitive dust emissions.

BACKGROUND OF THE INVENTION

Dust dissemination poses safety, health and environmental problems in many commercial environments. For example, in many industries, the transportation, handling and storage of bulk solids is common as in industries such as mining, mineral processing, agriculture, power, steel, paper production etc. One major problem associated with handling, transporting and storage of bulk solid is dust generation and the control of fugitive dust emissions.

In the mining and mineral processing area, fugitive dust emissions are a health and safety hazard that effects not only the site but also communities surrounding the mine area. Mining and transportation equipment is also affected by fugitive dust. Loading, hauling and conveying equipment experience down time due to maintenance associated with fugitive dust emissions. Fugitive dust emissions are a particular problem on mine/mineral processing site roads. Fugitive dust levels are usually high at such locations due to the activity levels and large area covered. Typical methods used to control fugitive dust on such roads are to use a tank truck to dispense water or a treatment chemical on the road surface. Treatment frequency can be based upon a predetermined schedule or on general observation of the area. Such treatment schedules are inefficient and often result in over or under treatment. Over treatment incurs costs with no benefit and under treatment can adversely impact the entire operation or the regulatory compliance of the site.

SUMMARY OF THE INVENTION

The present invention relates to an automated method of dust suppression. The method employs one or more dust monitors, a control means that implements a control algorithm, and a chemical feed system which comprises one or more dust treatment chemical application apparatus. In general, the method comprises measuring dust levels of an area with one or more dust level monitors which communicate the dust measurement to a central control system. The central control system implements a dust control/suppression algorithm that determines the need for application of dust control/suppression chemicals. The central control system then communicates the need for dust control/suppression treatment to the dust control treatment equipment that will apply the appropriate treatment.

This concept has utility in many industries, especially the mining and mineral processing area. Fugitive dust in the mining industry is a health and safety hazard that effects not only the site, but also communities surrounding the mine area. Mining equipment is also affected by fugitive dust; loading, hauling, and conveying equipment experience downtime due to maintenance associated with fugitive emissions.

The method of the present invention provides for an efficient use of resources by replacing a random or rigid schedule dust control system with an automated monitoring and treatment system. The automated monitoring and treatment system of the present invention integrates one or more dust level monitors, a central control means, and automated treatment chemical application equipment. The method comprising placing dust monitor(s) in an area where dust control is needed. The monitor(s) measure the dust levels in the area and communicate fugitive dust level information to the central control means. The central control means then evaluates the information using an algorithm. The algorithm determines the appropriate level and timing of a response that will provide the desired level of dust control/suppression and activates the automated dust control chemical feed equipment. The chemical feed equipment will apply dust control/suppression treatment to minimize the fugitive dust in that particular area.

Some operations such as ore crushing activities are localized generators of dust. Within the crushing facility dust monitors might be connected through electrical cable to the central control unit. The automated dust suppression chemical treatment application apparatus could also be connected to the central control unit via cables that provide power and communication.

Some operations require a special approach due to the distance between where the monitor(s), central control means, and automated treatment equipment are located. For example, a mining operation might have 20 miles of haul road that requires dust level monitoring and dust suppression treatment. Monitors would be required at some interval, such as every mile. Therefore, for a 20 mile haul road, 20 instruments might be specified to monitor dust levels at various points and communicate the dust level information to the central control processor. Conventional wiring would not be economical or safe in this type of widespread operation. Therefore, wireless modes of communication can be employed to establish communication between the dust level monitors, the central control means and the automated chemical treatment application equipment. Acceptable wireless communications methods can include spread spectrum, local mine frequencies, or global positioning systems (GPS) type systems. It is also expected, that in most such widespread situations, conventional power will not be available at each monitoring/treatment location. In such situation, the use of sensors, application equipment and system algorithms which provide efficient power usage are desirable. For example, sensors that minimize sampling thus reducing power requirements can be employed.

In other situations, such as retrofitting a complex system or site for dust control treatment, instillation of cables can be costly and/or difficult. In such situation, the use of automated sensing, control and treatment application equipment which is interconnected via wireless communication means can provide efficient dust suppression.

While the present invention has been described with respect to particular embodiments thereof, it is apparent that numerous other forms and modifications of this invention will be obvious to those skilled in the art. The appended claims and this invention should be construed to cover all such obvious forms and modifications which are within the true spirit and scope of the present invention.

What is claimed is:

1. A method of supressing the dissemination of fugitive dust particles into the atmosphere from at least one dust producing site comprising:

a) locating dust level monitoring means at one or more dust producing sites;
b) locating automated dust control treatment application means at said one or more dust producing sites;
c) providing a centralized control means to receive signals from said dust level monitoring means representative of the fugitive dust levels at said one or more dust producing sites and sending a responsive signal to said automated dust control treatment application means to activate said automated dust control treatment application means; and whereby fugitive dust at said more than one fugitive dust producing sites is suppressed.

2. The method of claim 1, wherein said signal from said dust level monitoring means to said centralized control means is via hard wire.

3. The method of claim 1, wherein said signal from said dust level monitoring means to said centralized control means is via wireless means.

4. The method of claim 1 wherein said signal from said centralized control means to said automated dust control treatment application means is via hard wire.

5. The method of claim 1 wherein said signal from said centralized control means to said automated dust control treatment application means is via wireless means.

* * * * *